US009459204B2

(12) United States Patent
Widman et al.

(10) Patent No.: US 9,459,204 B2
(45) Date of Patent: Oct. 4, 2016

(54) METHOD AND APPARATUS FOR MEASURING THE WAVEFRONT OF AN OPHTHALMIC DEVICE

(71) Applicant: Johnson & Johnson Vision Care, Inc., Jacksonville, FL (US)

(72) Inventors: Michael Widman, Jacksonville, FL (US); Naveen Agarwal, I, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 908 days.

(21) Appl. No.: 13/764,366

(22) Filed: Feb. 11, 2013

(65) Prior Publication Data

US 2013/0307965 A1    Nov. 21, 2013

Related U.S. Application Data

(60) Provisional application No. 61/597,338, filed on Feb. 10, 2012.

(30) Foreign Application Priority Data

Feb. 7, 2013   (WO) ................. PCT/US13/25077

(51) Int. Cl.
   *G01B 9/00*     (2006.01)
   *G01N 21/41*    (2006.01)
   *G01M 11/02*    (2006.01)

(52) U.S. Cl.
   CPC .............. *G01N 21/41* (2013.01); *G01M 11/02* (2013.01); *G01B 9/00* (2013.01)

(58) Field of Classification Search
   CPC .............. G02B 1/043; G02B 27/0025; G02B 27/0037; G02B 27/4211; G02B 27/0075; G02B 27/4205; G02B 5/18; G02B 5/1828; G02B 5/1895; G02B 21/006; G02B 21/04; G02B 21/24; G02B 21/241; G02B 21/245
   See application file for complete search history.

(56) References Cited

U.S. PATENT DOCUMENTS

| | | | |
|---|---|---|---|
| 2004/0190428 A1 | 9/2004 | Ito et al. | |
| 2004/0222539 A1* | 11/2004 | Hagmann | B29C 31/041 264/1.32 |
| 2010/0047380 A1* | 2/2010 | Widman | B29D 11/00009 425/174.4 |
| 2010/0245761 A1* | 9/2010 | Widman | G02B 1/043 351/159.41 |

FOREIGN PATENT DOCUMENTS

WO   WO 2009/025848 A2    2/2009

OTHER PUBLICATIONS

International Search Report for PCT/US2013/025077 Date of Mailing Jul. 10, 2013.

* cited by examiner

*Primary Examiner* — Michael P Stafira

(57) ABSTRACT

This invention provides for a method and a wavefront measuring apparatus used to measure, in one or continuous measurements, one or more ophthalmic devices directly on a forming mandrel, in non-hydrated state and in a much faster way with high spatial resolution.

24 Claims, 8 Drawing Sheets

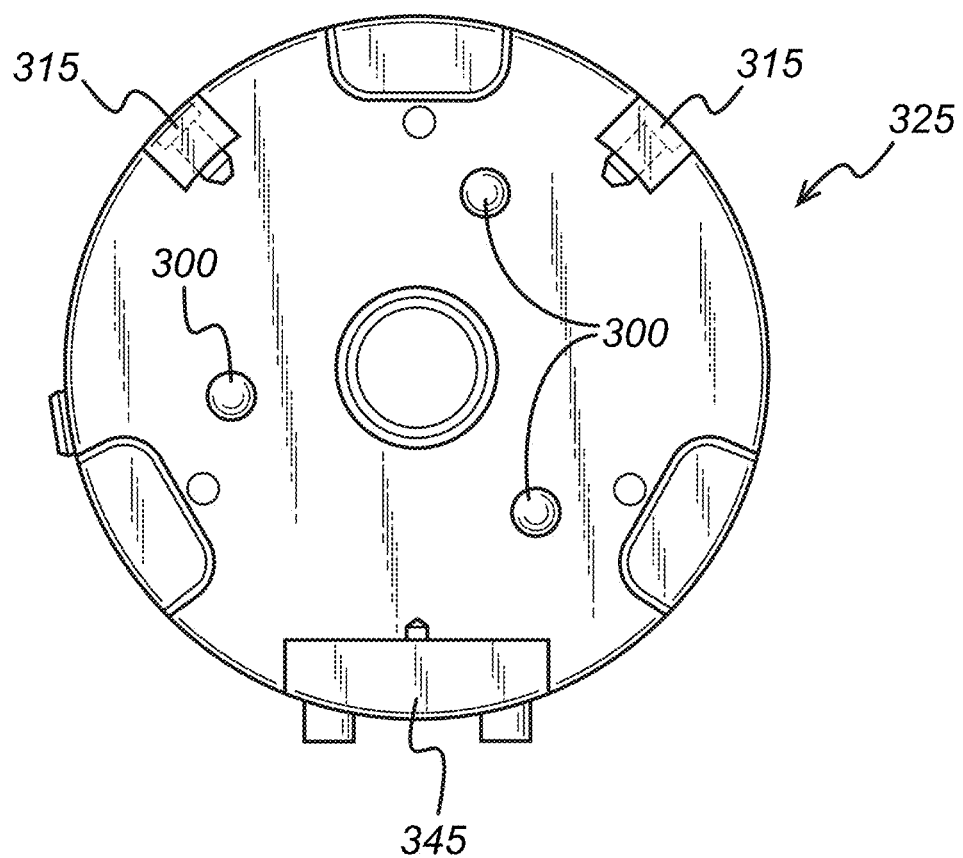
FIG. 3B
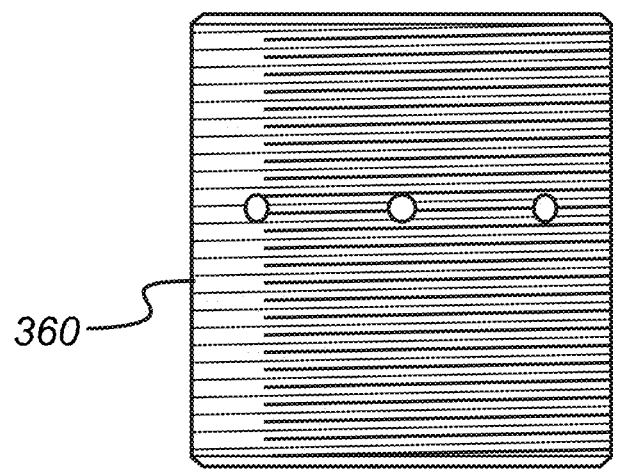

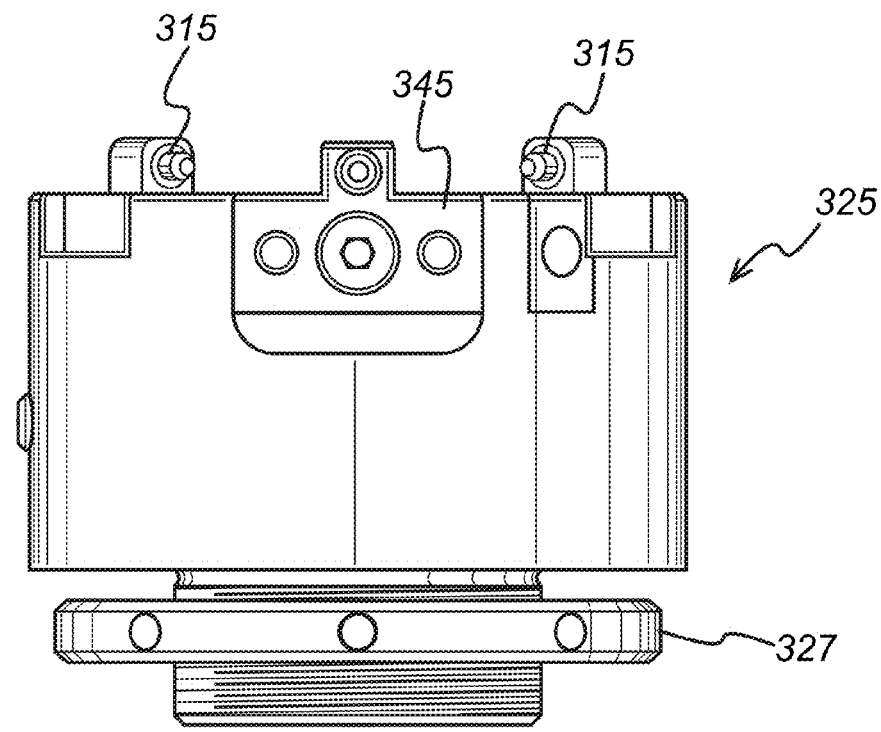
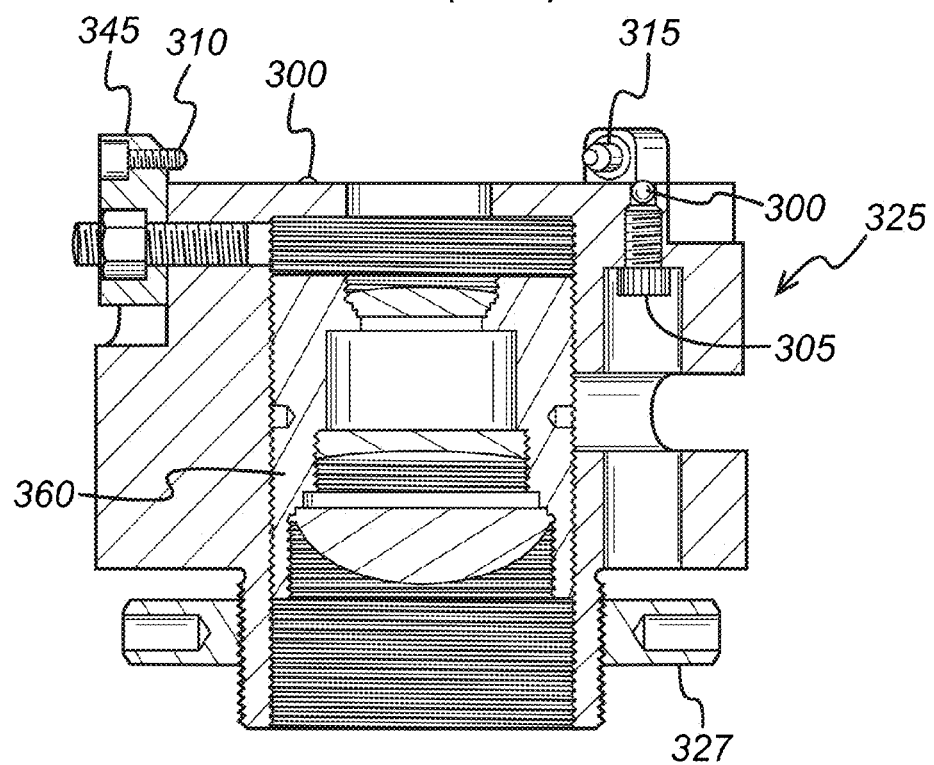
FIG. 3B(contd)

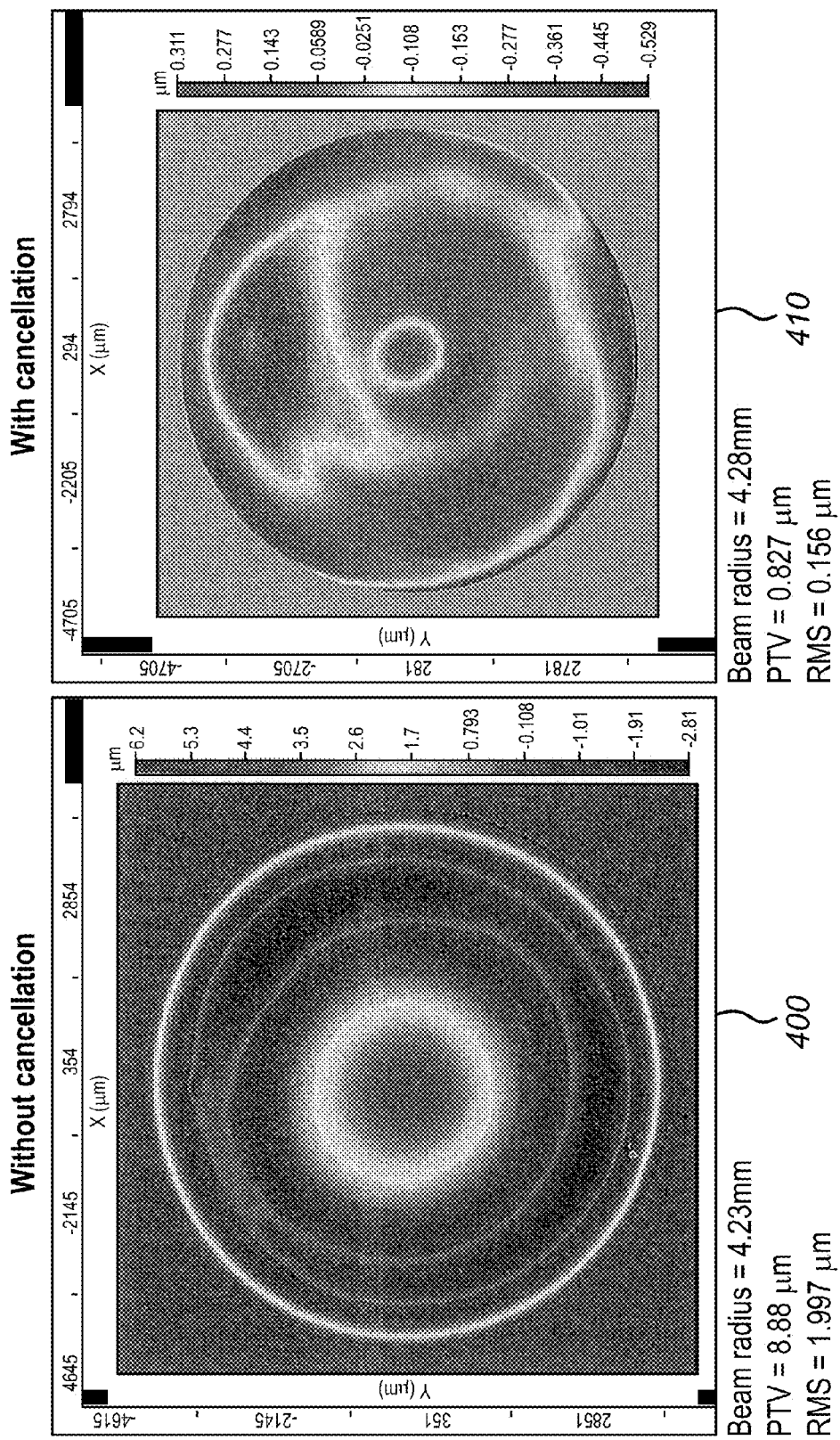

Custom Optic WF Measurement

420    Glass Mandrel + Lens
(Mandrel WF Removed)

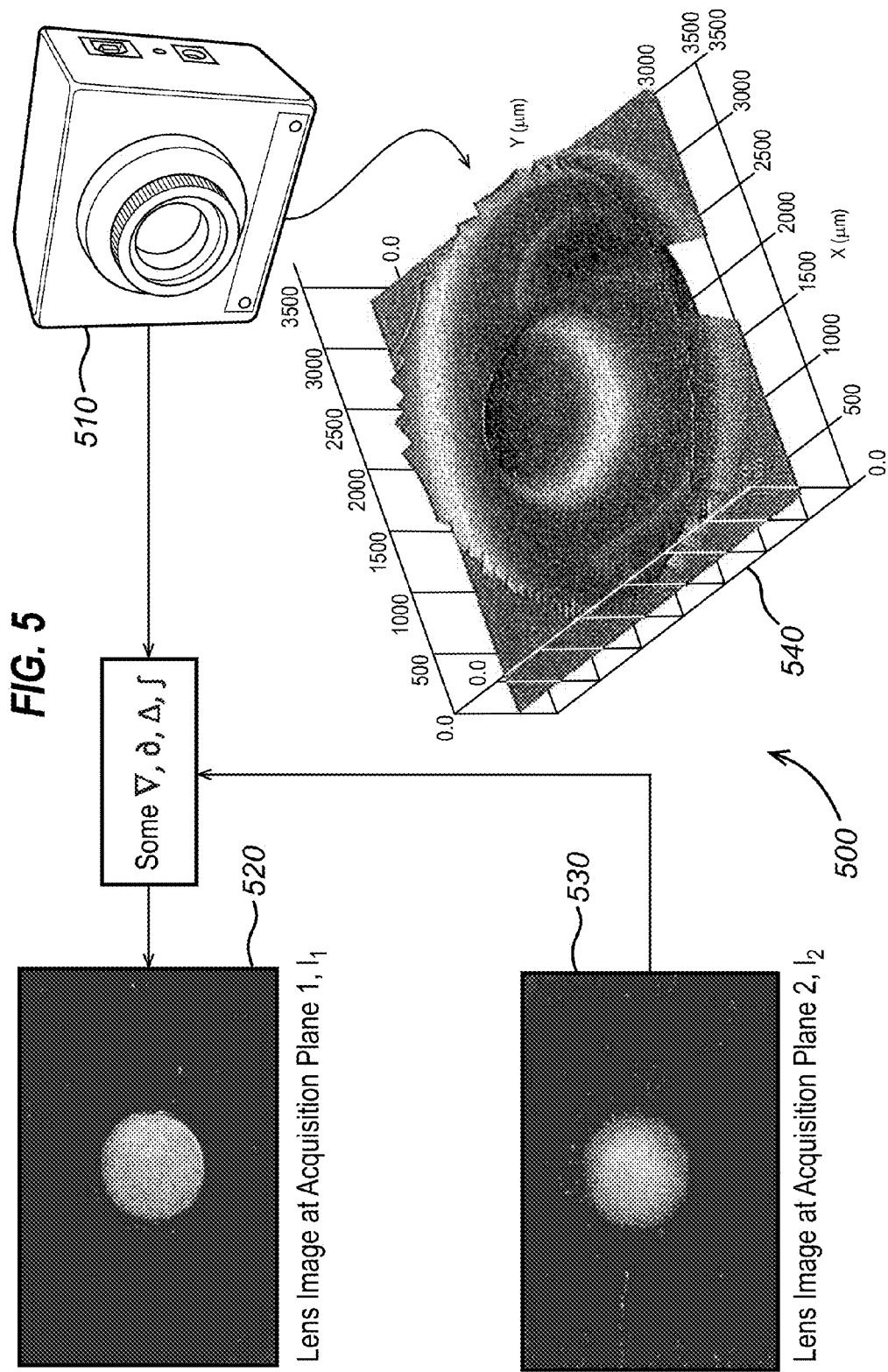

METHOD AND APPARATUS FOR MEASURING THE WAVEFRONT OF AN OPHTHALMIC DEVICE

RELATED APPLICATIONS

This application claims priority to the U.S. Provisional Application No. 61/597,338, filed Feb. 10, 2012, the contents of which are relied upon and incorporated herein.

FIELD OF USE

This invention describes a method and apparatus for obtaining accurate optical measurements of an ophthalmic device using an optical digital wavefront sensor and without contacting said ophthalmic device. More specifically, the apparatus uses an optical digital wavefront metrology technique to obtain simultaneous measurements of intensity and phase of the transmitted wavefront in one or more continuous measurements.

BACKGROUND OF THE INVENTION

It has been known to measure the physical properties of contact lenses using various devices and methods, i.e. optical metrology. Conventionally, optical metrology involves directing an incident beam at an optical object, measuring the resulting diffracted beam, and analyzing the diffracted beam to determine various characteristics, such as the profile of the structure. However, traditional ophthalmic lenses are often made by cast molding, in which a monomer material is deposited in a cavity defined between optical surfaces of opposing mold parts. To prepare a lens using such mold parts, an uncured hydrogel lens formulation is placed between a plastic disposable front curve mold part and a plastic disposable back curve mold part.

The front curve mold part and the back curve mold part are typically formed via injection molding techniques wherein melted plastic is forced into highly machined steel tooling with at least one surface of optical quality.

The front curve and back curve mold parts are brought together to shape the lens according to desired lens parameters. The lens formulation is subsequently cured, for example by exposure to heat and light, thereby forming a lens. Following cure, the mold parts are separated and the lens is removed from the mold parts for said conventional optical metrology. However, the nature of the injection molding processes and equipment make it difficult to form custom lenses specific to a particular patient's eye or a particular application. Consequently, in prior descriptions, methods and apparatus for forming customized lenses via the use of free-form techniques have been described, such as in WO 2009/025848 and WO 2009/025845. An important aspect of these techniques is that a lens is produced in a novel manner where one of two lens surfaces is formed in a free-form fashion without cast molding, lathing or other tooling.

A free formed surface and base may include a free flowing fluent media included in the free formed surface. This combination results in a device sometimes referred to as a lens precursor. Fixing radiation and hydration treatments may typically be utilized to convert a Lens Precursor into an ophthalmic lens.

A freeform lens created in this manner may need to be measured in order to ascertain the physical parameters of the lens. Therefore, new apparatus and methods are needed for measuring a lens formed from a precursor.

SUMMARY OF THE INVENTION

Accordingly, the present invention is directed to methods and apparatus for using a non-contact optical instrument for determining the measurement of an ophthalmic device, for example a dry contact lens that includes an UV-cured lens that has no moisture present in the lens, by using optical digital wavefront technology. Some key advantages of the present invention may include one or more of: a much faster way to obtain accurate measurements of dry contact lenses through single shot and real-time optical measurement, direct visualization of intensity and wavefront, a high dynamic range, a high spatial resolution as directly related to CCD camera resolution, vibration-insensitivity, and cost efficiency.

The present invention provides apparatus for measuring a physical characteristic of an ophthalmic device, the apparatus comprising:

an optic mandrel for forming an ophthalmic device using free-form technology; said optic mandrel comprising an optical effect;

a lens cancellation system comprising one or more lenses to collectively cancel said optical mandrel's optical effect;

an emitter functional to emit a wavelength of radiation in a direction towards the ophthalmic device;

a sensor functional to detect a transmitted wavefront based upon the emitted wavelength, wherein the transmitted wavefront's intensity and phase will be different based upon a physical characteristic of said ophthalmic device, and a processor in logical communication with one or both of the emitter and the sensor; wherein the processor is programmed to transmit a logical signal based upon the reflecting wavefront's intensity and phase.

The apparatus may measure more than one physical characteristic. Preferably, the apparatus obtains wavefront measurements of an ophthalmic device.

As used herein, the term "emitter" may mean "light source".

The optic mandrel, the lens cancellation system, the emitter and the sensor may be aligned. Preferably, the lens cancellation system, the emitter and the sensor are mounted on a rail. The rail may be a vertical rail, preferably a vertical optical rail.

In the apparatus, the sensor may comprise a digital wavefront camera. The digital wavefront camera may be capable of moving to change or vary continuously a distance along an optical axis of transmission of two or more intensity profiles. The digital wavefront camera may be vibration insensitive. The digital wavefront camera may further comprise a beam splitter to cause a production of a second image at a different position along the optical axis of transmission. Alternatively or in addition, the digital wavefront camera may further comprise one or more magnification lenses dependant on the diaphragm in a light source and the working distance between the light source and the digital wavefront camera.

The apparatus may further comprise a kinematic mount for placement of said optical mandrel for proper alignment with the lens cancellation system and the emitter. In addition, the apparatus may further comprise a vacuum for holding the mandrel fixture and the kinematic mount.

The apparatus may further comprise a top aperture and a bottom aperture, wherein said top aperture is slightly smaller than the bottom aperture and placed on top of the mandrel fixture without contacting said mandrel to create a physical barrier by limiting the light beam passing through defining a boundary condition for a solution of an intensity transport equation. The top aperture may be changed to cover a different field of view. The bottom aperture may also be changed to further improve a dynamic range of measurement.

The lens cancellation system used in the apparatus described herein may comprise an assembly comprising three lenses inside of a tube, wherein a light beam can pass through each of said lenses. The assembly may be placed perpendicularly to the rail. The light beam may be placed perpendicularly to the rail. The three lens cancellation system may include one or more of: an asphere lens, a plano-convex lens and a plano-concave lens to cancel out one or both of: defocus, and spherical aberrations of the forming optic mandrel which subsequently allows light coming out of the mandrel to be collimated.

The processor may function in real time to generate one or more continuous wavefront measurements of said ophthalmic device.

The emitted radiation may be a high quality light beam with a monochromatic wavelength. The emitted radiation may comprise a monochromatic wavelength of from about 630 nm to about 635 mm.

The present invention also provides a method of obtaining wavefront measurements of an ophthalmic device, the method comprising;

aligning an ophthalmic lens wavefront system, taking an optical measurement of a forming optic mandrel and storing that intensity measurement of a forming optic mandrel as an intensity reference file, taking an optical measurement of a forming glass mandrel with a lens that may have been formed on it and storing that intensity file, using software in a processor capable of subtracting one intensity file from at least one other intensity file to obtain a value for an optical wavefront of a lens in real time.

The method may further comprise a step of the processor implementing an intensity transport equation and an algorithm. Alternatively or in addition, intensity data may subsequently be converted into an optical wavefront. The optical wavefront may describe a path of light in terms of a light's intensity and phase.

The ophthalmic lens wavefront system used in the method of the present invention may comprise any of the apparatus described herein.

BRIEF DESCRIPTION OF THE DRAWINGS

FIG. 3, FIG. 3A, & FIG. 3B illustrate exemplary kinematic mount apparatus components that may be useful in implementing the present invention.

FIG. 4 illustrates an example of mandrel wavefront optical cancellation, as opposed to no mandrel wavefront optical cancellation.

FIG. 5 illustrates additional method steps that may be used to implement the present invention.

DETAILED DESCRIPTION OF THE INVENTION

Figure 1:
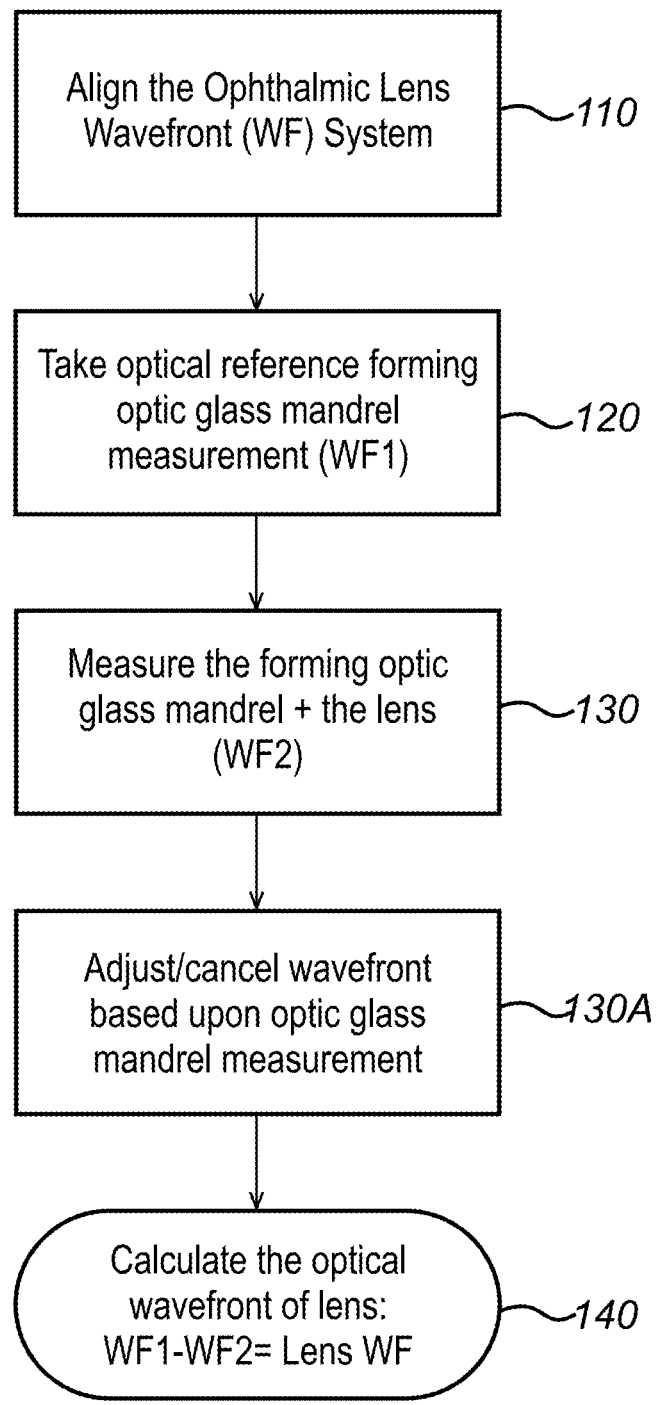
FIG. 1 illustrates method steps that may be used to implement the present invention.

The present disclosure provides for methods and apparatus for obtaining an optical wavefront measurement of an ophthalmic device. In the following sections, detailed descriptions of the invention will be given. The description of both preferred and alternative embodiments though thorough are exemplary only, and it is understood to those skilled in the art that variations, modifications, and alterations may be apparent. It is therefore to be understood that the exemplary embodiments do not limit the broadness of the aspects of the underlying invention as defined by the claims.

GLOSSARY

As used herein, the term "comprising" encompasses "including" as well as "consisting" and "consisting essentially of" e.g. an apparatus "comprising" X may consist exclusively of X or may include something additional e.g. X+Y.

"Fluent lens reactive media" as used herein means a reactive mixture that is flowable in either its native form, reacted form, or partially reacted form and, a portion or all reactive media may be formed upon further processing into a part of an ophthalmic lens.

"Free-form" as used herein refers to a surface that is formed by crosslinking of a reactive mixture via exposure to actinic radiation on a voxel by voxel basis, with or without a fluent media layer, and not shaped according to a cast mold, lathe, or laser ablation.

"Lens forming mixture" and sometimes referred as "reactive mixture" or "RMM"(reactive monomer mixture) herein refers to a monomer or prepolymer material which may be crosslinked to form an ophthalmic lens. Lens-forming mixtures may comprise one or more additives such as: UV blockers, tints, photoinitiators or catalysts, and other additives one might desire in an ophthalmic lenses such as, contact or intraocular lenses.

"Lens precursor" as used herein, refers to a composite object consisting of a lens precursor form and a fluent lens reactive mixture in contact with the lens precursor form. For example, the fluent lens reactive media may be formed in the course of producing a lens precursor form within a volume of reactive mixture. Separating the lens precursor form and adhered fluent lens reactive media from a volume of reactive mixture used to produce the lens precursor form may generate a lens precursor. Additionally, a lens precursor may be converted to a different entity by either the removal of significant amounts of fluent lens reactive mixture or the conversion of a significant amount of fluent lens reactive media into non-fluent, incorporated material.

"Lens precursor form" as used herein, means a non-fluent object with at least one optical quality surface which is consistent with being incorporated, upon further processing, into an ophthalmic lens.

"Ophthalmic lens" as used herein and sometimes referred to as "ophthalmic device" or "lens" refers to any ophthalmic device that resides in or on the eye. These devices can provide optical correction or may be cosmetic. For example, the term "lens" can refer to a contact lens, intraocular lens, overlay lens, ocular insert, optical insert or other similar device through which vision is corrected or modified, or through which eye physiology is cosmetically enhanced (e.g., iris color) without impeding vision. The preferred lenses of the invention may be soft contact lenses made from silicone elastomers or hydrogels, which include but are not limited to silicone hydrogels, and fluorohydrogels.

Measurements of one or more ophthalmic devices may be taken in its unhydrated lens state, and on a mandrel on which, a lens may be formed using free-form technology.

Included in the present disclosure are a digital wavefront camera and an objective lens. Also included, may be a mandrel fixture which may be mounted on a kinematic mounting device assembly that may include a three-lens mandrel cancellation system inside of a tube, a bottom aperture underneath, a mandrel fixture and a top aperture that is placed directly on top of the glass mandrel without making physical contact, a light source, a pinhole, diaphragm, and an asphere lens located in the bottom part of the apparatus. All of these components may be mounted perpendicularly to a vertical optical rail and adjusted, until the output beam from a light source is parallel with a rail and may be collimated as it exits the forming optic mandrel. Collimating light may be a parallel beam of light that has a flat wavefront, which means that the intensity of light does not change along an optical axis (referred to as "z direction").

A series of steps may be implemented to measure the free-formed unhydrated ophthalmic lenses. First, an optical measurement of a forming optic glass mandrel may be taken in transmission mode without a lens on it to obtain the optical wavefront of a base mandrel. That wavefront data may subsequently be stored as a reference file. A lens may subsequently be made on the same exact mandrel fixture which may be mounted onto said kinematic mount assembly. Subsequently, an optical measurement of a forming optic glass mandrel with a lens on it may be taken, in transmission mode and that wavefront data file may also be stored. The two data files may be subtracted from each other, thereby giving an optical wavefront measurement of a lens in transmission. Measurements may be made in transmission mode, but alternatively or in addition taking a measurement in reflective mode may be equally possible.

Referring now to FIG. 1, is a flow chart that illustrates method steps that may be used to obtain an optical wavefront of a lens. Various steps may include one or more of: aligning an ophthalmic lens wavefront (WF) system 110, followed by taking an optical wavefront measurement of a forming optic glass mandrel and storing that wavefront data as a reference file (wavefront 1) 120, followed by taking an optical wavefront measurement of a forming optic glass mandrel with a lens that may have been formed on that particular optic and storing that wavefront data file (wavefront 2) 130, followed by subtracting a wavefront 2 file from a wavefront 1 file and obtaining a value for an optical wavefront of an ophthalmic lens 140.

Figure 2:
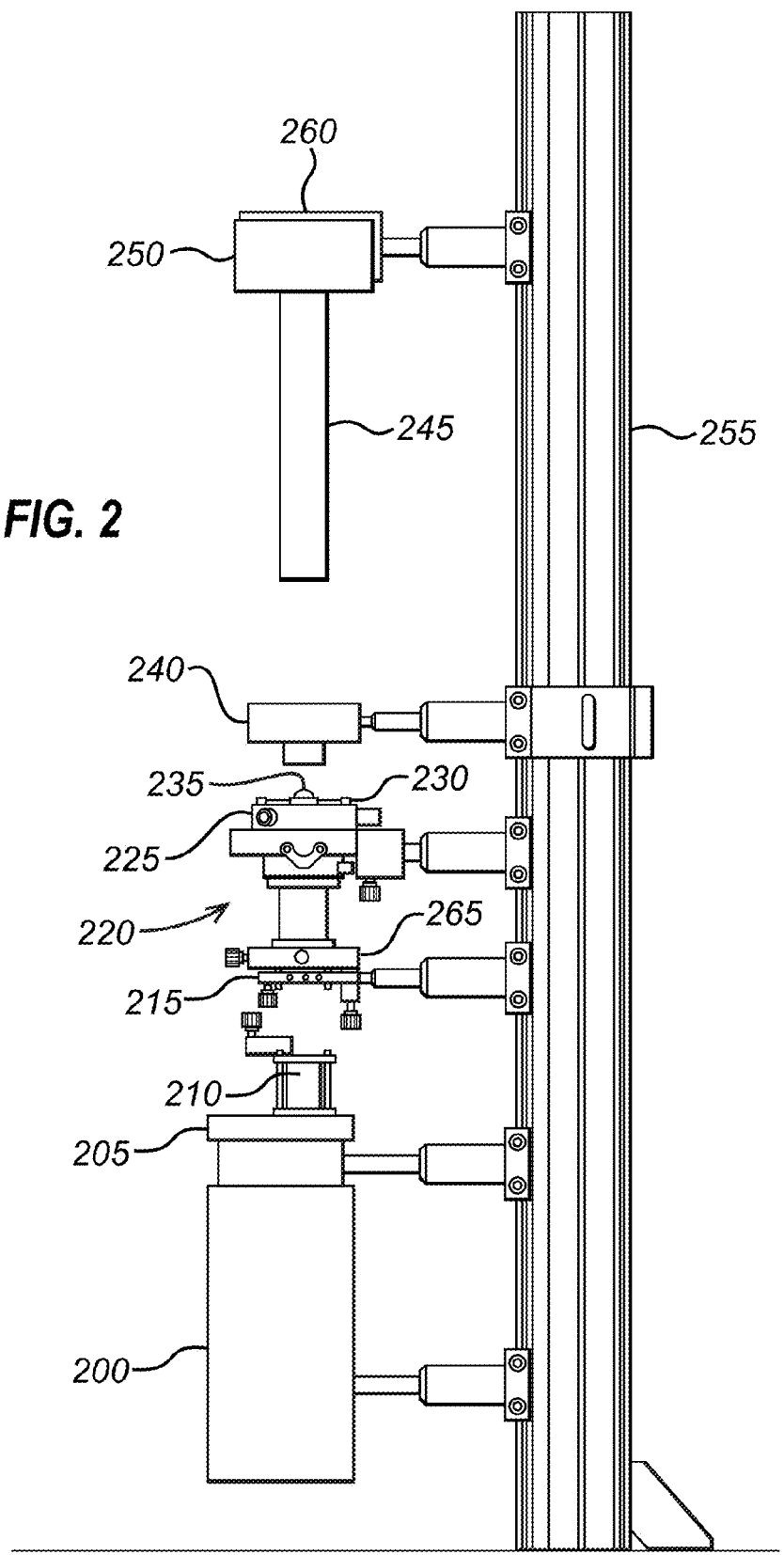
FIG. 2 illustrates apparatus components that may be useful in implementing the present invention comprising digital optical wavefront technology.

Referring now to FIG. 2, a side view of an exemplary wavefront measurement system mounted perpendicularly to a vertical optical rail 255 is depicted. A light source 200 may act as a reference for remaining components when aligning an apparatus and may be placed approximately 125 mm from a vertical optical rail 255. An overall objective purpose of aligning an apparatus may be so a collimated light beam may be produced parallel to a rail 255 when it exits a forming optic glass mandrel 235. A light source 200, which may have a wavelength of about 633 nm, may contain various optical elements inside and generate a high quality light beam. However, wavelength may vary, 633 nm is described herein for illustrative purposes but any other monochromatic wavelength may be used. A pinhole 205, which adjusts the diameter of the light beam, may restrict an uncollimated beam of light. An aspheric focusing lens 210 subsequently focuses a beam of light and collimates it. Before a collimated beam enters a mandrel cancellation optical system 220, there may be a bottom aperture 215 that may sit directly above an aspheric focusing lens 210 and may be mounted either independently or to the bottom of a "LP1A" (Axis adjustable) stage 265. An adjustable bottom aperture 215 controls a diameter of a collimated light coming from an aspheric focusing lens 210. A purpose of a bottom aperture 215 may be to restrict a field of view to allow a homogenous and uniform intensity profile and prevent saturation of a digital wavefront camera (also referred hereon as "DWC") 250.

Just above a bottom aperture 215 may be a kinematic mounting device 225, which may contain a tube inside of it comprising a series of lenses, which may collectively form a mandrel cancellation optical system 220. For example, a set of three lenses may be used: an asphere lens, a plano-convex lens, and a plano-concave lens. A purpose of a mandrel cancellation optical system 220 may be to cancel out both defocus and spherical aberration of a forming optic glass mandrel 235, which subsequently allows light coming out of a mandrel 235 to be collimated. Where there are three lenses of a mandrel cancellation optical system 220, the power and distances between the three lenses may be designed in such a way to cancel out an optical effect of a mandrel 235 in a 10 mm field of view, thereby causing the DWC to detect a flat wavefront. Otherwise, an optical effect of a mandrel 235 may introduce errors in calculation of a lens wavefront upon subtracting. Directly above a mandrel cancellation optical system 220 may be a kinematic mounting device 225 for the mandrel fixture 230 which may be mounted on top.

Figure 3:
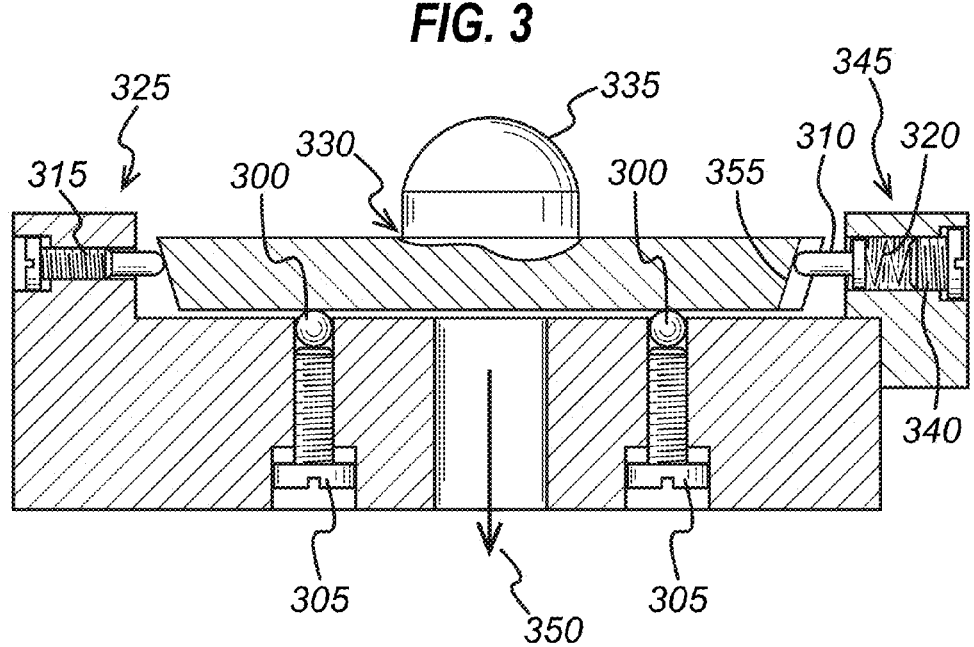
Figure 3A:
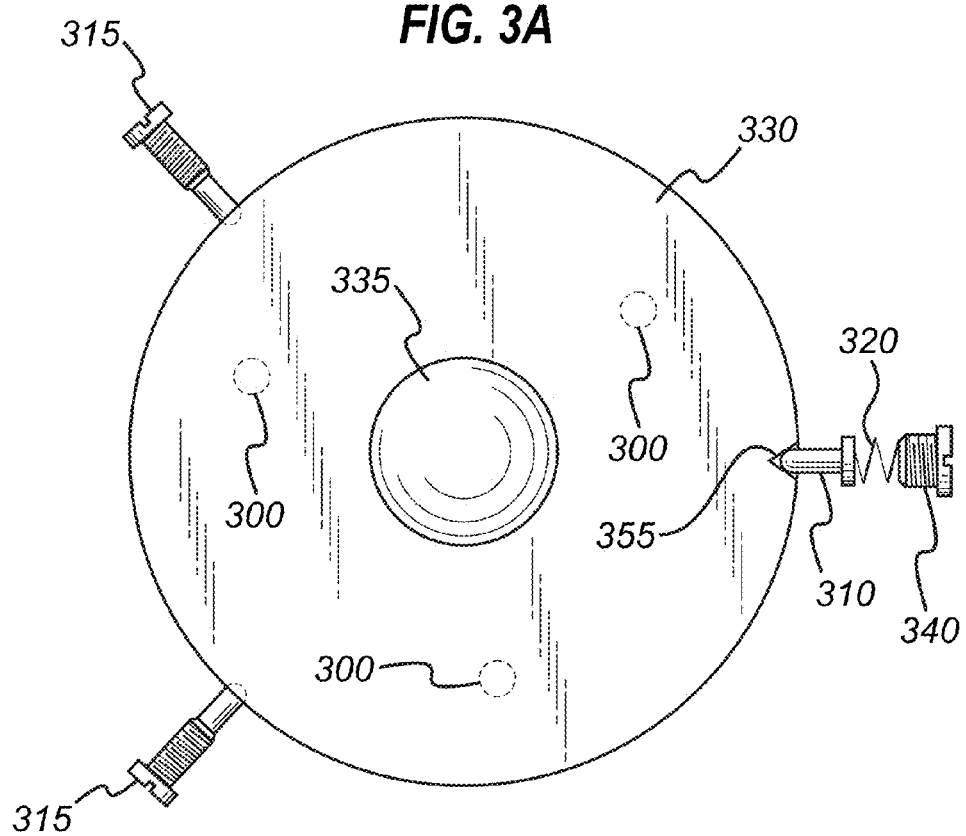

Referring now to both, FIG. 3 and FIG. 3A, FIG. 3 a schematic view of an exemplary kinematic mounting device assembly 325 is depicted. FIG. 3A represents a top view of a kinematic mounting device assembly 325. A forming optic assembly glass mandrel fixture 330 may be held in place by two adjuster ball pins 315 (only one of which is illustrated in FIG. 3) and a plunger 310. A plunger 310 rides in a grove that may have a spring 320 behind it, which may be captivated by spring pin assembly screw 340 representing a spring pin assembly 345. A plunger 310 may move in and out freely, engaging a mandrel fixture 330 in a notch 355. A notch 355 may keep a mandrel fixture 330 clocked in a desired position when a spring 320 pushes a plunger 310 into a notch 355. A spring pin assembly 345 via a plunger 310, pushes a mandrel fixture 330 towards the left (in FIG. 3), an edge of which subsequently impinges on adjuster ball pins 315. Adjustment of either of adjuster ball pins 315, may adjust an entire X,Y position of a mandrel fixture 330. Height and level of a mandrel fixture 330 may be adjusted by adjusting screws 305 and locating balls 300. A vacuum 350 may be applied to a space between a mandrel fixture 330 and a kinematic mount 325. A vacuum 350 holds a mandrel fixture 330 down onto the balls 300, but not to a point that a spring 320 and plunger 310 may be inhibited from pushing a mandrel fixture 330 against adjuster ball pins 315. A forming optic glass mandrel 335 may be positioned on a mandrel fixture 330. Different geometries of a kinematic mounting device 325 may be used.

Referring now to FIG. 3B, represents a broken view of a kinematic mounting device 325 and an encapsulating lens tube 360 that houses three lenses of a mandrel cancellation optical system. Also illustrated, may be a location of a mandrel cancellation optical system contained inside of a kinematic mount 325. The kinematic mounting device 325 may comprise a locking nut 327.

Referring back to FIG. 2, a top aperture 240 may be attached to a rail 255 directly above a mandrel fixture 230. A top aperture 240 may be placed directly on top of a mandrel fixture 230 as close to a forming optic glass mandrel 235 without actually physically touching it. Different geometries of a top aperture 240 may be used. A top aperture 240, which may be slightly smaller than a bottom aperture 215, may restrict a diameter of a collimated light beam exiting a forming optic glass mandrel 235, causing a DWC 250 only to get intensity from a collimated light in only a certain zone restricted by a top aperture 240. A top aperture 240 diameter may be changed to cover a different field of view. A purpose of a top aperture, may be to create a physical barrier by limiting light to pass through only that aperture which defines a boundary condition for a solution of an intensity transport equation, which assumes that an intensity of light outside of a diameter of a top aperture 240 may be equal to zero. An adjustable top aperture 240, or various combinations of a top aperture 240 and bottom aperture 215 may be used to improve a dynamic range of measurement.

An objective lens 245 may sit directly above a top aperture 240 and a DWC 250 may be attached to an objective lens 245. A DWC 250 may be mounted on an X, Y stage 260. Alternatively, a rotation stage may be mounted here. Inside of a DWC there may be a beam splitter which may cause a second intensity image at a fixed distance along the optical axis of transmission from a first intensity image to be formed. Distance between two images may be changed to another fixed value or varied continuously using a movable camera. A working distance between a DWC 250 and a diaphragm in a light source 200 may be dependent upon an objective camera lens magnification used. An objective lens camera magnification may be 0.333 and working distance may be 69 mm.

There may be three alignment positions of a DWC 250. First, a DWC 250 and objective lens 245 may be positioned on a vertical optical rail 255 in position 1. In position 1, an objective lens 245 images a top aperture 240 in a DWC 250, which produces a first image in focus, referred to as image 1. Second, a DWC 250 and objective lens 245 may be positioned down on a vertical optical rail 255 in position 2, in which image 1 becomes fuzzy. In position 2, a beam splitter in a DWC 250 may subsequently cause a production of a second image, referred to as image 2. Finally, a DWC 250 and objective lens 245 may be subsequently positioned in between image 1 and image 2, in a final position. In a final position, image 1 and image 2 may be both equally fuzzy.

Figure 4A:
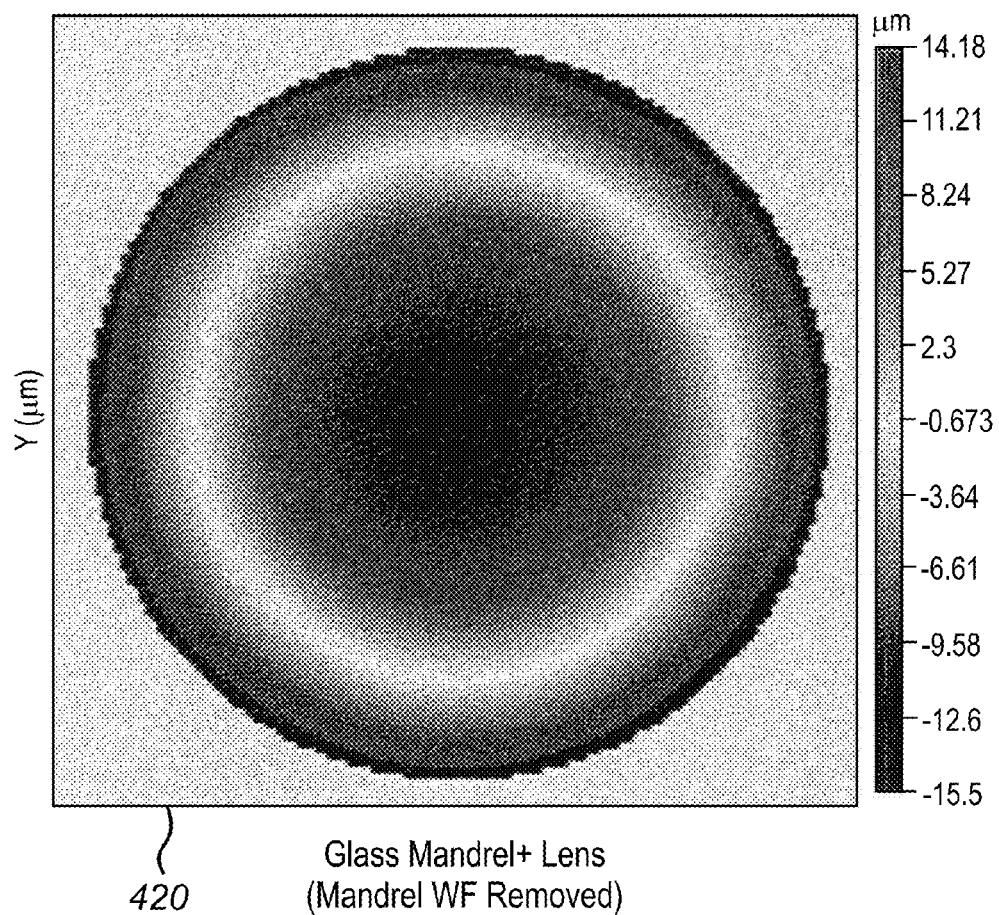
FIG. 4A illustrates an example of a dry lens wavefront after mandrel wavefront optical cancellation.

Referring now to both FIG. 4 and FIG. 4A, FIG. 4 is an example of a computer generated optical wavefront of a reference without mandrel optical cancellation 400 and an optical wavefront of a reference mandrel with mandrel optical cancellation 410. FIG. 4A illustrates an example of a computer generated wavefront of a dry lens obtained after removing a mandrel optical wavefront 420. After a system has been aligned, a first measurement taken may be an optical reference measurement of a glass mandrel without a lens on it, shown as example 410. That data may be referred to as wavefront 1 and may be stored. A second optical measurement may subsequently be taken of a glass mandrel with a lens on it and that data which is referred to as wavefront 2, may be stored. Finally, wavefront 1 may be digitally subtracted from wavefront 2 to yield a lens wavefront, shown as an example in 420.

Referring now to FIG. 5, represents a picture diagram 500 to illustrate a process by which the wavefront measurement 540 may be done through acquisition of image 1 520 and image 2 530 from a DWC 510. During a measurement, two intensity images, image 1 520 and image 2 530 may be obtained. The software utilized may be referred to as Getwave software (version 1.0.9) designed by Phaseview. However, other software may be used that performs the same function. For illustration purposes, image 1 520 may be referred to as intensity distribution 1 and image 2 530 as intensity distribution 2. These two intensity distribution images may subsequently be used in a calculation, which may be made inside of software, based upon the difference between the two images. Subsequently, an optical wavefront may be constructed for a measurement. More specifically, software utilizes a generic equation, which may be referred to as the intensity transport equation, the equation which is:

$$-\kappa \frac{\partial \theta_Z}{\partial z} I_Z(r) = \underbrace{I_Z(r)\nabla^2 \phi_Z(r)}_{Curvature} + \underbrace{\nabla I_Z(r) \cdot \nabla_Z(r)}_{Slope}$$

The intensity transport equation may be implemented in such a way by using a particular algorithm, to allow for a measurement of a glass mandrel or a glass mandrel with a lens on it and to collect intensity data from both measurements. Intensity data may subsequently be converted into an optical wavefront. An optical wavefront describes a path of light in terms of a light's intensity and phase. A wavefront may be measured in terms of one or more of: Zernike coefficients, as peak to valley ("PTV"), and wavefront root mean square ("RMS"), as compared to flat wave. Subsequent to wavefront calculations for both a reference measurement of a glass mandrel without a lens (wavefront 1) and a measurement of a glass mandrel with a lens (wavefront 2); two wavefront files, wavefront 2 and wavefront 1, may be subtracted from one another to obtain a value for an optical wavefront of a lens.

CONCLUSION

The present disclosure, as described above and as further defined by the claims below, provides methods and apparatus for measuring physical characteristics of one or more ophthalmic devices.

The invention claimed is:
1. Apparatus for measuring a physical characteristic of an ophthalmic device, the apparatus comprising:
   an optic mandrel for forming an ophthalmic device using free-form technology; said optic mandrel comprising an optical effect;
   a lens cancellation system comprising one or more lenses to collectively cancel said optical mandrel's optical effect;
   an emitter functional to emit a wavelength of radiation in a direction towards the ophthalmic device;
   a sensor functional to detect a transmitted wavefront based upon the emitted wavelength, wherein the transmitted wavefront's intensity and phase will be different based upon a physical characteristic of said ophthalmic device, and
   a processor in logical communication with one or both of the emitter and the sensor; wherein the processor is programmed to transmit a logical signal based upon the reflecting wavefront's intensity and phase.
2. The apparatus of claim 1 wherein the optic mandrel, the lens cancellation system, the emitter and the sensor are aligned.

3. The apparatus of claim 1 or claim 2 wherein the optic mandrel, the lens cancellation system, the emitter and the sensor are mounted on a rail.

4. The apparatus of claim 3, wherein the rail is a vertical optical rail.

5. The apparatus of any of the preceding claims wherein the sensor comprises a digital wavefront camera.

6. The apparatus of claim 5 wherein the digital wavefront camera is capable of moving to change or vary continuously a distance along an optical axis of transmission of two or more intensity profiles.

7. The apparatus of claim 5 or claim 6 wherein the digital wavefront camera is vibration insensitive.

8. The apparatus of any of claims 5 to 7 wherein the digital wavefront camera further comprises a beam splitter to cause a production of a second image at a different position along the optical axis of transmission.

9. The apparatus of any of claims 5 to 8 wherein the digital wavefront camera further comprises one or more magnification lenses dependant on the diaphragm in a light source and the working distance between the light source and the digital wavefront camera.

10. The apparatus of any of the preceding claims further comprising a kinematic mount for placement of said optical mandrel for proper alignment with the lens cancellation system and the emitter.

11. The apparatus of claim 10 further comprising a vacuum for holding the mandrel fixture and the kinematic mount.

12. The apparatus of any of the preceding claims further comprising a top aperture and a bottom aperture, wherein said top aperture is slightly smaller than the bottom aperture and placed on top of the mandrel fixture without contacting said mandrel to create a physical barrier by limiting the light beam passing through defining a boundary condition for a solution of an intensity transport equation.

13. The apparatus of claim 12 wherein said top aperture can be changed to cover a different field of view.

14. The apparatus of claim 12 or claim 13 wherein said bottom aperture can also be changed to further improve a dynamic range of measurement.

15. The apparatus of any of the preceding claims wherein said lens cancellation system comprises an assembly comprising three lenses inside of a tube, wherein a light beam can pass through each of said lenses and may be placed perpendicularly to the rail.

16. The apparatus of claim 15 wherein said three lens cancellation system can include one or more of: an asphere lens, a plano-convex lens and a plano-concave lens to cancel out one or both of: defocus, and spherical aberrations of the forming optic mandrel which subsequently allows light coming out of the mandrel to be collimated.

17. The apparatus of any of the preceding claims wherein the processor functions in real time to generate one or more continuous wavefront measurements of said ophthalmic device.

18. The apparatus of any of the preceding claims wherein the emitted radiation is a high quality light beam with a monochromatic wavelength.

19. The apparatus of any of the preceding claims wherein the emitted radiation comprises a monochromatic wavelength of from about 630 nm to about 635 mm.

20. A method for obtaining wavefront measurements of an ophthalmic device, the method comprising;
aligning an ophthalmic lens wavefront system,
taking an optical measurement of a forming optic mandrel and storing that intensity measurement of a forming optic mandrel as an intensity reference file,
taking an optical measurement of a forming glass mandrel with a lens that may have been formed on it and storing that intensity file,
using software in a processor capable of subtracting one intensity file from at least one other intensity file to obtain a value for an optical wavefront of a lens in real time.

21. The method of claim 20 further comprising the processor implementing an intensity transport equation and an algorithm.

22. The method of claim 20 or claim 21 wherein intensity data may subsequently be converted into an optical wavefront.

23. The method of claim 22 wherein the optical wavefront describes a path of light in terms of a light's intensity and phase.

24. The method of any of claims 20 to 23, wherein the ophthalmic lens wavefront system comprises the apparatus of any of claims 1 to 19.

\* \* \* \* \*